United States Patent [19]

White

[11] 4,008,270
[45] Feb. 15, 1977

[54] PROCESS FOR PREPARING 2-(SUBSTITUTED PHENYL)PROPIONIC ACIDS

[75] Inventor: David R. White, Kalamazoo, Mich.
[73] Assignee: The Upjohn Company, Kalamazoo, Mich.
[22] Filed: Oct. 14, 1975
[21] Appl. No.: 622,130
[52] U.S. Cl. .................. 260/515 R; 260/515 A; 260/514 K; 260/514 R
[51] Int. Cl.$^2$ .................................. C07C 63/04
[58] Field of Search .............. 260/515 R, 515 A
[56] References Cited

UNITED STATES PATENTS 3,852,286  12/1974  Hall et al. ..................... 260/515 A
3,880,916  4/1975   Dickel et al. ................. 260/515 A

FOREIGN PATENTS OR APPLICATIONS 1,265,800  3/1972  United Kingdom ........... 260/515 R

OTHER PUBLICATIONS

House, *Modern Synthetic Reactions*, W. A. Benjamin Inc., Menlo Park, Calif., pp. 595–599 (1972).

*Primary Examiner*—James O. Thomas, Jr.
*Assistant Examiner*—G. T. Breitenstein
*Attorney, Agent, or Firm*—John T. Reynolds

[57] ABSTRACT

Preparing 2-(substituted phenyl)propionic acids by heating a mixture containing succinic acid anhydride with a 2-(2-oxo-3-cyclohexenyl)propionic acid derivative and then recovering the 2-(2-substituted phenyl)propionic acid derivative from the reaction mixture. The heated mixture can also contain other acids such as an 2-(1-carboxy-2-oxo-3-cyclohexenyl)propionic acid.

10 Claims, No Drawings

PROCESS FOR PREPARING 2-(SUBSTITUTED PHENYL)PROPIONIC ACIDS

INTRODUCTION

This invention relates to processes for preparing 2-(2-substituted phenyl)propionic acids. More particularly, this invention provides an efficient method for converting 2-(2-oxo-3-cyclohexenyl)propionic acid derivatives to the corresponding 2-(substituted phenyl)propionic acid.

BACKGROUND OF THE INVENTION

In the last several years a number of 2-(substituted phenyl)alkanoic acid derivatives have been discovered and developed for use as anti-inflammatory, analgesic and anti-pyretic drugs, for use in treating mammals, including humans. Many of these drugs are described in the medicinal and patent literature. Examples of the more significant of such compounds which are being commercialized or studied for possible commercialization and which can be prepared by the process of this invention include 2-(4-isobutylphenyl)propionic acid, now known generically as ibuprofen, 2-(2-fluoro-4-phenylphenyl)propionic acid, now known generically as flurbiprofen (see U.S. Pat. No. 3,755,427) and 2-(4-phenylphenyl)propionic acid, and a number of others.

A number of chemical process routes have been described for making these alkanoic acid derivative drug compounds. Most of such processes have involved the use of aromatic ring moiety reactants. For example, processes have been described for preparing the 2-(substituted phenyl)propionic acids (a) from aromatic clycidonitriles (see Argentine Pat. Nos. 198,097 and 198,595), (b) from aromatic glycidyl esters (see German Offenlegungsshrift No. 2,404,159, published Aug. 29, 1974), (c) from aromatic alkyl cyanides and by a variety of other process routes, all of which involve the use of an aromatic moiety. See, for example, U.S. Pat. 3,600,437 for a description of a number of those processes.

More recently Belgian Pat. No. 820,267 described a process for preparing p-isobutyl-hydratropic acid (ibuprofen) by treating an aliphatic compound of the formula

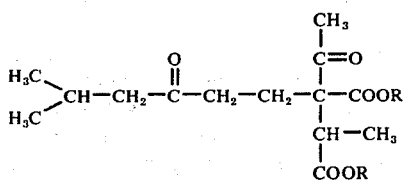

where each R is a $C_1$ to $C_5$-alkyl, with a strong acid aqueous solution at 200 to 240° C., or in a dry state with a strong acid salt and an organic base for from 30 minutes to 3 hours. That Belgian Patent also indicates that its formula (II) compound need not be isolated before acid treatment but can be obtained in the crude product form by reacting the vinyl-isobutyl-ketone with alkyl α-acetyl-α-methylsuccinate, or by reaction of an acetoacetic acid ester with an alkyl α-halopropionate and then with the vinyl-isobutyl-ketone.

That Belgian Patent also refers to prior processes and to some prior patents, including British Patent No. 1,265,800 which is said to disclose the synthesis of methyl or ethyl 2-(4-isobutyl-2-oxocyclohex-3-enyl)-propionate in some undisclosed yield. The Belgian Patent No. 820,267 indicates that when they repeated the pertinent experiments of the British Pat. No. 1,265,800 they obtained yields of less than 5 percent; and concluded the process for preparing p-isobutyl-hydratropic acid (ibuprofen) as described in British Pat. No. 1,265,800 had no industrial application. The Belgian Pat. points out that the advantages of its described process for preparing 2-(4-isobutyl-2-oxo-3-cyclohexenyl)propionic acid intermediate is that it does not require the use of expensive and dangerous reagents such as silver nitrate or cyanide ion. That Belgian Pat. process for the production of ibuprofen from 2-(4-isobutyl-2-oxo-3-cyclohexenyl)propionic acid is based upon the aromatization which occurs when a dialkyl-α-acetyl-α-[(5-methyl-3-oxo)hexyl]-α'-methylsuccinate is heated to temperatures of about 200 to 240° C. with strong acid, but the Belgian Pat. process requires the use of a polmerizable intermediate.

The British Pat. No. 1,265,800 process requires the use of corrosive materials. Persons skilled in this process art are searching for improved processes for making these valuable drug compounds while avoiding the use of polymerizable intermediates or corrosive materials.

OBJECTS OF THE INVENTION

It is an object of this invention to provide an improved process for preparing a 2-(2-substituted phenyl)propionic acid compound from a 2-(2-oxo-3-cyclohexenyl)propionic acid derivative.

A more specific object of this invention is to provide an improved process for preparing a 2-(substituted phenyl)propionic acid from a mixture of acids containing a 2-(2-oxo-3-cyclohexenyl)propionic acid and a 2-(1-carboxy-2-oxo-3-cyclohexenyl)propionic acid.

A more specific and preferred object is to provide a process for preparing 2-(4-isobutylphenyl)propionic acid, also known as 4-isobutyl-hydratropic acid and by the generic name ibuprofen.

Other objects, advantages and aspects of this invention will be apparent from reading the remaining specification and the claims which follow.

SUMMARY OF THE INVENTION

According to this invention it has been discovered that certain 2-(substituted phenyl)propionic acid compounds can be prepared by forming a mixture containing a non-acidic dehydrating agent which is stable at the heating temperatures and a compound selected from the group consisting of

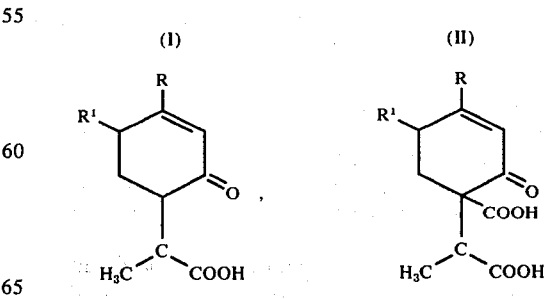

where R and $R^1$ are as defined below and a compound of the formula

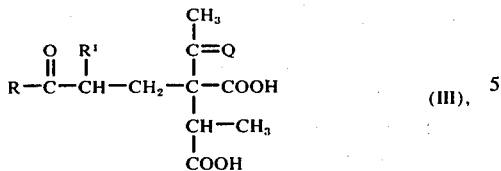

(III), heating the mixture to from about 150° C. to below the decomposition point of the formula IV acids (below) in the mixture until aromatization is essentially completed, and recovering the 2-(substituted phenyl)propionic acid from the resulting mixtures.

DETAILED DESCRIPTION OF THE INVENTION

More specifically, according to this invention I have discovered that 2-(substituted phenyl)propionic acid compounds of the formula

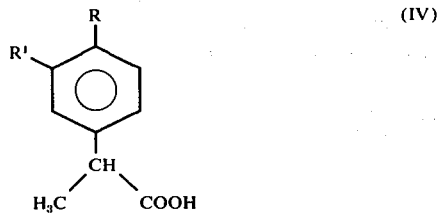

(IV)

where R is phenyl or $C_1$ to $C_6$-alkyl and $R^1$ is hydrogen or fluoro, which are pharmaceutically active drug compounds which are useful as part of the therapy to treat adnormal inflammatory, pain or fever conditions in mammals, including humans, can be prepared by (a) forming a mixture containing a non-acidic dehydrating agent which is stable at the heating temperature and at least one compound of formulas I, II and III above, (b) heating the mixture at from about 150° C. to below the decomposition point of the 2-(2-substituted phenyl)-propionic acid in the mixture, preferably at from about 180° C. to about 270° C., until analyses of samples of the reaction mixture indicate that aromatization of the starting materials I, II and III above to the phenylene ring is essentially or optimally completed, and (c) recovering the 2-(substituted phenyl)propionic acid from the resulting mixture.

In the heating step (b) the time needed to effect aromatization will vary depending upon the starting material, the choice of dehydrating agent and the heating temperature. In most combinations of these reactants and conditions the mixture will be heated for from about 1 to 48 hours. The lower heating temperatures around 150° C. will require longer heating times than the same mixture being heated at the higher, more preferred temperatures. With the preferred reactants, heating the mixture for from about 1 to about 10 hours is usually sufficient.

Examples of acid starting materials which can be used in this process include
2-(2-oxo-4-isobutyl-3-cyclohexenyl)propionic acid,
2-(1-carboxy-2-oxo-4-isobutyl-3-cyclohexenyl)propionic acid,
2-(2-oxo-5-fluoro-4-phenyl-3-cyclohexenyl)propionic acid.
2-(2-oxo-4-methyl-3-cyclohexenyl)propionic acid,
2-(2-oxo-4-hexyl-3-cyclohexenyl)propionic acid,
2-(1-carboxy-4-phenyl-3-cyclohexenyl)propionic acid,
2-(1-carboxy-5-fluoro-4-phenyl-3-cyclohexenyl)propionic acid, α-acetyl-α-(5-methyl-3-oxohexyl)-α'-methylsuccinic acid, α-acetyl-α-(2-fluoro)-2-benzoylethyl-α-methylsuccinic acid, and the like.

The starting materials can be prepared by reacting a Mannich base of the formula

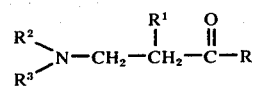

wherein R and $R^1$ are as defined above, and $R^2$ and $R^3$ denote the residue of the secondary amine used to make the Mannich base, with an α-acetyl-α'-methyl-succinate ester in the presence of a deprotonating base, e.g., potassium carbonate, and an alkylating agent, e.g., dimethylsulfate, in an organic liquid solvent. Depending upon the amount of deprotonating base which is used in the mixture the products formed will be esters of acids of formulas I, II or III above. For example, if a substantial amount, say, about a molar equivalent of the base is used in the mixture the product mixture will be predominantly esters of the acids of formulas I and II above, that is, 2-(2-oxo-3-cyclohexenyl)propionic or 2-(1-carboxy-2-oxo-3-cyclohexenyl)propionic acid ester derivatives. If only a catalytic amount of base is used and the ketone derived from the Mannich base is a vinyl ketone the intermediate product will be predominantly an ester of the structure III acid. Use of intermediate amounts of base in the reaction mixture containing the vinyl ketones will produce mixtures of esters of formulas I and II and III above. Thereafter, these ester intermediates are recovered from the reaction mixture and hydrolyzed to the acids with acid or base for use of those acids as starting materials in the process of this invention. In addition to the above procedure the procedures described in British Pat. No. 1,265,800 can be used to make the preferred 2-(4-isobutyl-2-oxo-3-cyclohexenyl)propionic esters, 2-(1-carboxy-4-isobutyl-2-oxo-3-cyclohexenyl)propionate esters and the acids therefrom, and the procedure of Belgian Pat. No. 820,267 can used to make the ethyl α-acetyl-α-(5-methyl-3-oxo-hexyl)-α'-methyl succinate or other ester, from which the acid thereof can be obtained by known hydrolysis procedures.

The non-acidic dehydrating agents used in the reaction mixtures in the process of this invention should be stable at the temperatures to which the mixture is heated in this process. A variety of dehydrating aromatizing agents useful for this purpose are known compounds and include carbodiimide compounds such as di-($C_1$ to $C_8$-alkyl)carbodiimides, e.g., diethyl-, diisopropyl, diisopropyl, dipentylcarbodiimides, diphenylcarbodiimide, di-p-tolylcarbodiimide, dicyclohexylcarbodiimide, florisil, phenyl isocyanate as well as organic acid anhydrides such as anhydrides of $C_2$ to $C_6$-alkanoic acids such as acetic anhydride, propionic anhydride, butanoic anhydride, pentanoic anhydride, hexanoic anhydride as well as anhydrides of dicarboxylic acids such as succinic anhydride, phthalic anhydride, maleic anhydride, citraconic anhydride, n-butyric anhydride, n-valeric anhydride, benzoic anhydride, naphthalic anhydride, pyromellitic anhydride, diphenic anhydride, and the like.

When anhydrides boiling less than about 150° C. at atmospheric pressure are used as the dehydrating agents, the mixtures can be heated in a pressure vessel to raise the effective boiling point to the desired heating temperature of about 150° C. or higher. The choice of dehydrating agent will depend upon cost, availability, safety equipment availability, time of reaction desired, desired heating temperatures, and reactants involved. For reasons of availability, cost advantage and safety qualities, and the heating temperatures for most of the starting materials and products of this process, we prefer to use organic acid anhydrides, particularly succinic anhydride. The other dehydrating agents can be used but they are too expensive, or they give a more complex mixed acid product which we prefer to avoid.

The mixture containing the compound of formula I, II or III, above, or mixture of these starting materials and the non-acid dehydrating agent can be prepared dry and then heated to about 150° C. or higher until aromatization is completed in the product mixture, or the starting material acid (formulas I, II or III above) can be added to a warmed, melted or boiling dehydrating agent. Alternatively, the starting materials and the dehydrating agent can be mixed in a boiling inert, organic liquid which will form a solution or suspension of those reactants during the heating step. Examples of organic liquids which can be used for this purpose include diphenyl ether, and the like. Alternatively organic acids such as succinic acid can be heated with substrate; the organic acid dehydrates to the organic anhydride due to heat and then performs its function of dehydration. The dehydration of the organic acid occurs faster than the aromatization of the starting material so that the aromatizing agent is the anhydride. In most of such mixtures, whether the reactants are mixed neat or with a diluting medium, the dehydrating agent is used in an amount which is at least stoichiometrically equivalent to the acids in the mixture which are to be aromatized. The dehydrating agent is usually used in excess molar amounts to ensure complete aromatization. We have found that it is usually sufficient to use from 2 to 10 molar equivalents of the dehydrating agent relative to the acid content to effect substantially complete aromatization in a reasonable time, say, 1 to 4 hours. In any event the mixture is usually heated at from about 150° C. to below the decomposition points of the acids in the mixture, preferably at from about 180° to 270° C., until analysis of samples of of the reaction mixture indicates that aromatization to the phenylene ring is essentially or optimally complete. The desired 2-(2-substituted phenyl)propionic acid can be recovered from the reaction mixture by known procedures. For example, the reaction vessel and its contents can be cooled to below the boiling point of water, preferably near to room temperature and mixed with an alkali metal base aqueous solution, say, from 5 to 15 percent concentration, and stirred or otherwise agitated to hydrolyze the anhydrates contained therein.

The base treated mixture can then be diluted with non-water miscible organic liquid to separate components not soluble in the aqueous base pH phase and stirred for a time to effect good mixing. Suitable organic liquids for this purpose include toluene, xylene, heptane, carbon tetrachloride, Skellysolve B and the like. In this way neutral impurities are removed in the organic phase. After acidification of the aqueous phase the 2-(2-substituted phenyl)propionic acid is extracted with an organic solvent whereas the water soluble component, e.g., succinic acid, remains in the aqueous phase. After separating of the phases the organic phase can be evaporated to concentrate and to crystallize the crude 2-(2-substituted phenyl)propionic acid product which can then be further purified by conventional methods. For example when ibuprofen is being prepared by this method the crude acid product can be redissolved in a solvent such as Skellysolve B and recrystallized therefrom by evaporation of the solvent.

By the process of this invention substantial yields of the desired 2-(substituted phenyl)propionic acid can be obtained without the need to use highly corrosive materials or to generate polymerizable intermediates. The invention is further exemplified by the detailed preparations and examples which are not intended to limit the scope of the invention.

PREPARATION 1

A. Preparing Mixture containing ethyl 2-(4-isobutyl-2-oxo-cyclohex-3-enyl)propionate (II) and ethyl 2-(1-carboethoxy-4-isobutyl-2-oxo-cyclohex-3-enyl)-propionate (I)

To an oven dried 3-necked flask there was added 10.0 ml. of absolute ethanol, and the flask and its contents were cooled to 0° C. Then 264 mg. (11 millimoles) of sodium hydride was added slowly under a nitrogen atmosphere to form sodium ethoxide. After solution was attained, 2.53 g. (11 millimoles) of diethyl 2-acetyl-3-methyl succinate and 1.85 g. (10 millimoles) of the Mannich base adduct of isobutyl methyl ketone and diethylamine were added. Then 2.52 g. (20 millimoles) of dimethylsulfate was added over five minutes while holding the temperature of the mixture below 5° C. After stirring the cooled reaction mixture for 4 hours, the temperature of the mixture was allowed to rise to room temperature while stirring for an additional 16 hours. To insure complete reaction the mixture was cooled again to 0° C. and 264 mg. (11 millimoles) of sodium hydride was added to the mixture. Then the mixture was stirred for an additional 1 hour as the temperature was allowed to rise to room temperature (about 20° C.).

The resulting reaction mixture was then concentrated to an oil, diluted with 30 ml. of ethyl acetate and 10 ml. of 10 percent sulfuric acid in water. The aqueous and organic phases were separated and the upper organic phase was washed with 10 ml. of brine solution. After drying and concentration 4.03 g. of an oil remained. Gas liquid chromatography (glc.) and mass spectrum analyses of samples of this oil showed that it contained:

33 percent diethyl 2-acetyl-3-methylsuccinate (starting material)
5 percent diethyl 2-acetyl-3-methylsuccinate (which had been methylated on the oxygen), and
12.5 percent of 2-(4-isobutyl-2-oxo-cyclohex-3-enyl)propionic acid (I) ethyl ester and
38 percent 2-(1-carboethoxy-4-isobutyl-2-oxo-cyclohex-3-enyl)propionic acid (II);, ethyl ester.

The oil was chromatographed on silica gel and eluted with a 15:85 v/v mixture of ethyl acetate and Skellysolve B to give 1.52 g. of ethyl 2-(1-carboethoxy-4-isobutyl-2-oxo-cyclohexenyl)-propionate (II) ester containing some ethyl 2-(4-isobutyl-2-oxo-cyclohex-3-enyl)propionate (I) ester as an oil:

Infrared (CHCl$_3$): 3022, 2985, 1732 1673, 1637, 1473 1381, 1254, 1200 cm$^{-1}$.

NMR (CDCl$_3$): 352 (s, 1H), 248 (2 quartets, 4H), 202 (m, 1H), 160–105 (m, 7H) 73 (t, 9H), 53 Hz (two doublets, 6H).

Mass spectrum: 325 (M + 1), 309, 289, 266, 251, 236, 235, 224, 232, 82

B. A chromatographed 1 gm. mixture of ethyl 2-(4-isobutyl-1-carboethoxy-2-oxocyclohex-3-enyl)propionate and ethyl 2-(4-isobutyl-2-oxocyclohex-3-enyl)-propionate was dissolved in ethanol (4.0 ml.) and then 5.5 ml. of 1 N sodium hydroxide solution was added. The resulting mixture was stirred at 40° C. for 20 hours and then concentrated to about 7 ml. volume. The aqueous residue was extracted with 5 ml. of Skellysolve B and the extract was backwashed with 3 ml. of 1 N sodium hydroxide. The aqueous phases were combined and acidified, extracted as before, dried and concentrated to give an oil, 0.672 g. This oil product consisted of 2-(4-isobutyl-1-carboxy-2-oxocyclohex-3-enyl)propionic acid and 2-(4-isobutyl-2-oxo-cyclohex-3-enyl)-propionic acid. This was shown by taking gas liquid chromatographs (glc.) and mass spectra of portions of the product oil which had been converted to silyl esters and methyl esters.

PREPARATION 2:

Preparation of
2-(4-isobutyl-2-oxo-3-cyclohexenyl)propionic acid

To a flask containing absolute ethanol there was added 2.53 g. (11 millimoles) of diethyl α-acetyl-α-methylsuccinate, followed by 3.36 ml. of the Mannich base, N,N-diethyl-N-5-methyl-3-oxo-hexylamine and anhydrous potassium carbon at (4.17 g.). Then after cooling the mixture to 0° C., 2.74 ml. of dimethyl sulfate was added over 20 minutes. The mixture was then allowed to warm to room temperature and it was stirred at that temperature for 15 hours. An additional 1.10 ml. of the Mannich base was added and the mixture was stirred for an additional 8 hours to insure complete reaction.

Then 1.5 ml. of a 50 percent sodium hydroxide solution in water was added and the mixture was stirred. After 6 hours a second 0.5 ml. of the sodium hydroxide was added. After an additional hour of stirring the solvent was distilled off and the residue was treated with 26 ml. of water and 25 ml. of benzene. The aqueous layer was separated and acidified with sulfuric acid and extracted with Skellysolve B to obtain 3.25 g. of acidic products. Chromatography of the acidic products on silica gel gave 195 milligrams of pure 2-(4-isobutyl-2-oxo-3-cyclohexenyl)propionic acid and 1.963 g. of a less pure batch of this acid.

Analysis of the pure acid gave the following readings.

Infrared (neat): 3520–2400 br, 2480 2890, 1717, 1676, 1641, 1475, 1382, 1300, 1252, 1226 cm$^{-1}$.

Nuclear Magnetic Resonance (NMR) (CDCl$_3$): 363 (s, 1H), 352 (S, 1H), 95–180 (m, 7H), 70 (t, 3H), 56 Hz (d, 6H).

Mass Spectrum (of trimethylsilyl ester): 297 (M + 1), 296 (M$^+$), 281, 253, 223, 179, 152, 146, 131, 130, 82, 75, 73.

PREPARATION 3

Preparation of (I)
2-(4-isobutyl-2-oxocyclohex-3-enyl)propionic acid

A mixture of potassium iodide (0.5 g.)., potassium carbonate (100 mmole; 13.8 g.) and ethanol (15 ml.) was cooled to 10° C. Ethyl acetoacetate (75 mmole, 9.51 ml.) and ethyl bromopropionate (75 mmole, 9.22 ml.) were added and the stirred mixture was brought to 70° C. After 3.25 hours at that temperature the mixture was cooled to room temperature. Ethanol (45 ml.) potassium carbonate (156 mmoles, 21.5 g.) and 23.0 ml. of crude (about 90% pure) Mannich base (made from diethylamine, formaldehyde and isobutyl methyl ketone, (92 mmoles) were added. Dimethyl sulfate (205 mmoles; 19.00 ml.) was added over 45 minutes with cooling so the temperature was less than 16° C. The mixture was stirred at 20° C. for 157 hours, 40° C. for 13.4 hours. The mixture was filtered and the solid was washed with 20, 15 and 10 ml. portions of ethanol.

One-half of the filtrate was concentrated to 35 ml. at reduced pressure and then diluted with 45 ml. of 1 sodium hydroxide solution. The resulting solution was stirred at 40° C. for 21 hours and then ethanol was evaporated and the residue was washed with toluene. After separating the aqueous phase from the toluene phase the aqueous phase was acidified with sulfuric acid, extracted with toluene, washed with brine and concentrated to an oil which weighed 7.40 gm. This oil can be used to prepare the mixture with the dehydrating aromatizing agent according to this invention. However, to analyze the content of the oil for identification purposes, the oil was placed on silica gel and eluted with a mixture of Skellysolve B/benzene/ethanol/acetic acid (55:40:45:0.5 v/v). Crystallization of the appropriate fractions gave 2-(4-isobutyl-2-oxo-cyclohex-3-enyl)propionic acid which was identical (by infrared spectrum) with a reference standard sample of the same compound.

EXAMPLE 1

In a 5 ml. flask there was mixed 150 mg. of 2-(4-isobutyl-2-oxo-3-cyclohexenyl)propionic acid and 450 mg. of succinic anhydride. The flask was placed in a 150° C. oil bath and heated to 205° C. over 20 minutes and held at 205° C. for 30 minutes. The heating temperature was then raised to 244° C. over 1 hour. After another hour at 244° C. to insure complete reaction the reaction mixture flask was cooled and stirred with 16 ml. of 10 percent sodium hydroxide in water solution for 1.5 hours. A 195 mg. portion of solid product containing 2-(4-isobutylphenyl)propionic acid, sublimed from the flask. Toluene (10 ml.) was added to the residue and the mixture was stirred for an hour. The phases were separated and the toluene layer was washed with 6 ml. of 0.1N sodium hydroxide. The basic phases were washed in sequence with 7 ml. portions of toluene to remove 58 mg. of neutral material. The combined aqueous layers were added to 1.0 ml. of Skellysolve B and acidified with 8 ml. of 10 percent sulfuric acid. The aqueous layer was removed and extracted again with 7 ml. of Skellysolve B and then the Skellysolve B phases were washed were 8 ml. and 5 ml. portions of warm water to remove succinic acid. The Skellysolve B phase was evaporated to give 51.5 mg. of crude ibuprofen, 2-(4-isobutylphenyl)propionic acid. Recrystallization of the crude ibuprofen from 0.8 ml. of Skellysolve B gave 16.3 mg. of purified ibuprofen, m.p. 71.5°–74.5° C. The infrared spectrum of this ibuprofen was identical to that of a reference standard ibuprofen sample.

EXAMPLE 2

Following the procedure of Example 1 but replacing the succinic anhydride, with an excess amount of phthalic anhydride, and in which the mixture was heated at 275° C. for 80 minutes, then 310° C. for 10 minutes produces an acid product which contains ibuprofen (2-(4-isobutylphenyl)propionic acid) mixed with other acid components.

EXAMPLE 3

The acid, 2-(5-fluoro-4-isobutyl-2-oxo-3-cyclohexenyl)propionic acid is prepared following generally the procedure of Preparation 2, by reacting 2-fluoromethyl isobutyl ketone with formaldehyde and N,N-diethylamine hydrochloride to form the Mannich base, N,N-diethyl-N-(2-fluoro-5-methyl-3-oxo-hexyl) amine. This Mannich base is reacted with diethyl α-acetyl-α-methylsuccinate in the presence of dimethyl sulfate in ethanol, and the resulting product is converted to the acid by the above described procedure.

Then, following the procedure of Example 1, the 2-(5-fluoro-4-isobutyl-2-oxo-3-cyclohexenyl)propionic acid is mixed with a stoichiometric excess of succinic anhydride and heated to effect aromatization and form 2-(3-fluoro-4-isobutylphenyl)propionic acid, which is a known compound having anti-inflammatory properties which is useful as a drug to treat abnormal inflammatory conditions in mammals, including humans.

EXAMPLE 4

The acid, 2-(5-fluoro-4-phenyl-2-oxo-3-cyclohexenyl)propionic acid is prepared by reacting 2-fluoromethyl phenyl ketone with formaldehyde and N,N-diethylamine hydrochloride to form the Mannich base, N,N-diethyl-N-(2-fluoro-3-oxo-3-phenylpropyl)amine. This Mannich base is reacted with diethyl α-acetyl methylsuccinate in the presence of dimethylsulfate in ethanol, and the resulting product is converted to the acid by the above described procedures.

Then, following the procedure of Example 1, the 2-(5-fluoro-4-phenyl-2-oxo-3-cyclohexenyl)propionic acid is mixed with a stoichiometric excess of succinic anhydride and heated to effect aromatization and form the 2-(3-fluoro-4-phenyl)propionic acid which is a known acid having anti-inflammatory properties which is useful as a drug to treat abnormal inflammatory conditions in mammals, including humans.

I claim:
1. Process for preparing a 2-(substituted phenyl)propionic acid of the formula

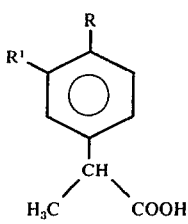

(IV)

wherein R is phenyl or $C_1$ to $C_6$-alkyl and $R^1$ is hydrogen or fluoro, which comprises a. forming a mixture containing a dehydrating agent which is stable at the heating temperature and is selected from the group consisting of di($C_1$ to $C_6$-alkyl)carbodiimides, diphenylcarbodiimide, di-p-tolylcarbodiimide, dicyclohexylcarbodiimide, florisil, phenylisocyanate and organic acid anhydrides and at least one compound having a formula selected from the group consisting of

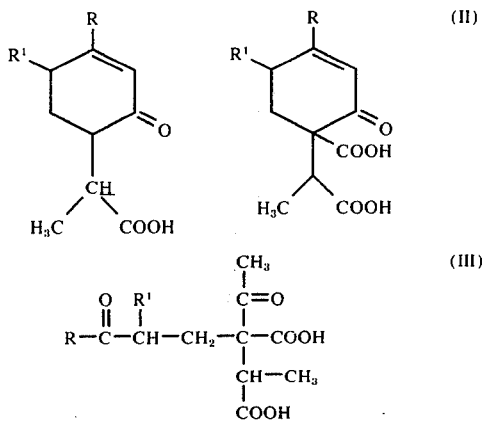

wherein R and $R^1$ are as defined above b. heating the mixture from step (a) to from about 150° C. to below the decomposition point of the formula IV acid until aromatization has occurred, and (c) recovering the 2-(substituted phenyl)propionic acids from the resulting mixture.

2. Process of claim 1 wherein the dehydrating agent is an organic acid anhydride.

3. Process of claim 2 wherein the dehydrating agent is a saturated aliphatic acid anhydride.

4. Process of claim 3 wherein the dehydrating agent is succinic anhydride.

5. Process according to claim 1 for preparing ibuprofen which comprises (a) forming a mixture containing a dehydrating agent which is stable at the heating temperature and at least one compound selected from the group consisting of
2-(4-isobutyl-2-oxo-3-cyclohexenyl)propionic acid,
2-(1-carboxy-4-isobutyl-2-oxo-3-cyclohexenyl)propionic acid, and
α-acetyl-α-(5-methyl-3-oxohexyl)-α'-methylsuccinic acid,
(b) heating the mixture from step (a) to from about 150° C. to below the decomposition point of ibuprofen until aromatization is completed, and (c) recovering ibuprofen from the resulting mixture.

6. Process according to claim 5 wherein the dehydrating agent is an organic acid anhydride.

7. Process of claim 6 wherein the dehydrating agent is a saturated aliphatic acid anhydride.

8. Process according to claim 7 wherein the dehydrating agent is succinic anhydride.

9. Process according to claim 5 for preparing ibuprofen which comprises (a) forming a mixture containing succinic anhydride and 2-(4-isobutyl-2-oxo-3-cyclohexenyl)propionic acid, (b) heating the mixture to from about 150° C. to below the decomposition point of ibuprofen in the mixture until aromatization is substantially complete, and recovering ibuprofen from the resulting mixture.

10. Process according to claim 9 wherein in step (a) the mixture also contains 2-(1-carboxy-4-isobutyl-2-oxo-3-cyclohexenyl)propionic acid.

* * * * *